(12) United States Patent  
Spector

(10) Patent No.: US 9,750,325 B1  
(45) Date of Patent: Sep. 5, 2017

(54) HAIR COLOR APPLICATOR

(71) Applicant: Donald Spector, New York, NY (US)

(72) Inventor: Donald Spector, New York, NY (US)

( * ) Notice: Subject to any disclaimer, the term of this patent is extended or adjusted under 35 U.S.C. 154(b) by 0 days.

(21) Appl. No.: 15/189,070

(22) Filed: Jun. 22, 2016

Related U.S. Application Data

(63) Continuation-in-part of application No. 15/073,841, filed on Mar. 18, 2016.

(60) Provisional application No. 62/335,830, filed on May 13, 2016, provisional application No. 62/295,679, filed on Feb. 16, 2016, provisional application No. 62/295,679, filed on Feb. 16, 2016.

(51) Int. Cl.
| | |
|---|---|
| *B43K 5/14* | (2006.01) |
| *A45D 34/04* | (2006.01) |
| *A45D 37/00* | (2006.01) |
| *A61M 35/00* | (2006.01) |
| *A46B 11/00* | (2006.01) |

(52) U.S. Cl.
CPC ......... *A45D 34/041* (2013.01); *A45D 34/042* (2013.01); *A45D 37/00* (2013.01); *A46B 11/0075* (2013.01); *A61M 35/003* (2013.01)

(58) Field of Classification Search
CPC  A45D 34/041; A45D 34/042; A46B 11/0075; A61M 35/003

USPC .................................................. 401/132–134
See application file for complete search history.

(56) References Cited

U.S. PATENT DOCUMENTS

| | | | |
|---|---|---|---|
| 5,778,902 A | 7/1998 | Nagy | |
| 5,937,866 A | 8/1999 | Magharehi | |
| 7,530,358 B2 | 5/2009 | Elliott | |
| 7,631,645 B2 * | 12/2009 | Gayton | A45D 19/02 132/112 |
| 8,061,917 B2 * | 11/2011 | Stenton | A61B 17/00491 401/133 |
| 8,820,333 B2 * | 9/2014 | Cristophe | A45D 19/02 132/221 |
| 9,629,990 B2 * | 4/2017 | Law | A61M 35/003 |
| 2008/0306439 A1 | 12/2008 | Nelson | |

* cited by examiner

*Primary Examiner* — Jennifer C Chiang  
(74) *Attorney, Agent, or Firm* — Collard & Roe, P.C.

(57) ABSTRACT

An apparatus for applying a two-component liquid composition to a surface has a housing having an open end, an inner surface and an outer surface, an applicator retained in the housing and projecting through the open end, two containers removably mounted to the inner surface of the housing, each container having a dispensing nozzle extending through an aperture in the housing and arranged adjacent the applicator. There is a cutting device arranged on the housing adjacent the nozzles, the cutting device having at least one blade, wherein pressing the cutting device causes the blades to pierce the nozzles and allow contents of the containers to exit the containers and flow to the applicator.

8 Claims, 6 Drawing Sheets

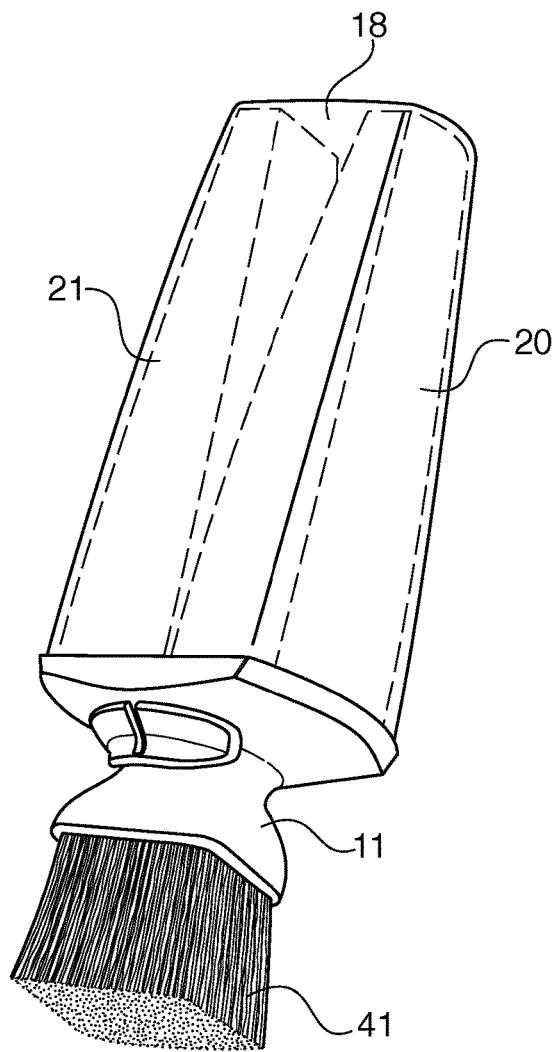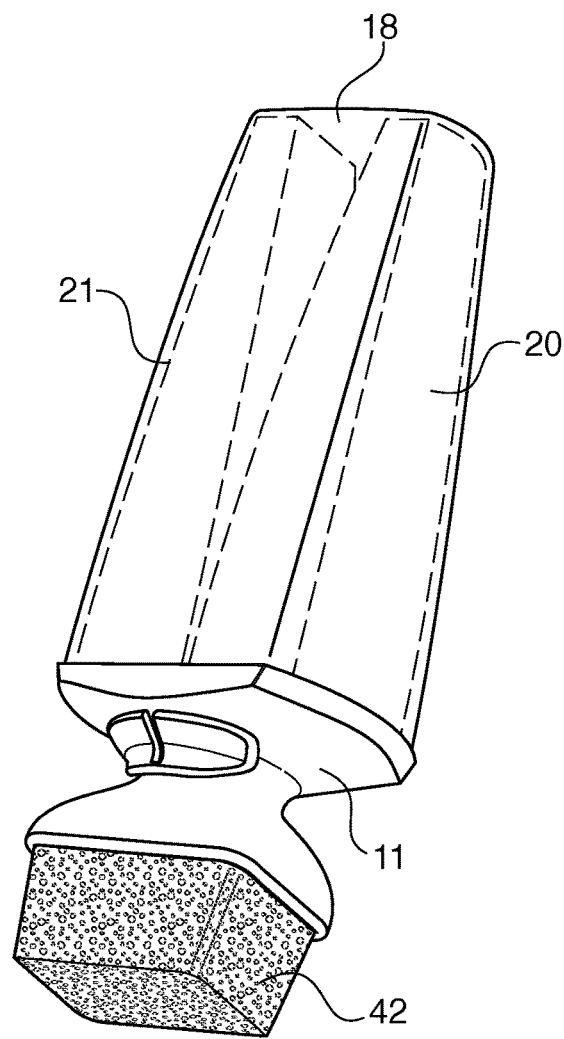
FIG. 9
FIG. 10

HAIR COLOR APPLICATOR

CROSS REFERENCE TO RELATED APPLICATIONS

This application claims priority under 35 U.S.C. §119(e) of U.S. Provisional Patent Application Nos. 62/335,830 filed on May 13, 2016 and 62/295,679 filed on Feb. 16, 2016. This application is also a continuation-in-part of U.S. patent application Ser. No. 15/073,841, filed on Mar. 18, 2016, which claims priority under 35 U.S.C. §119(e) of U.S. Provisional Patent Application Ser. No. 62/295,679 filed Feb. 16, 2016, the disclosures of all of which are incorporated by reference.

BACKGROUND OF THE INVENTION

1. Field of the Invention

This invention relates to an applicator for applying hair color or other liquid cosmetic to a person's hair or skin. In particular, the invention relates to an apparatus comprising two chambers for dispensing two different liquids simultaneously onto a roller ball or other applicator, which mixes the liquids and applies them to a surface or hair.

2. The Prior Art

Hair coloring is often applied using a flexible bottle with a nozzle, which sends liquid from the bottle directly onto the person's scalp by squeezing the bottle. Alternatively, the hair coloring can be applied by brushing the liquid onto the desired area with a brush or sponge. While both of these methods are effective in placing the liquid onto the surface, it is difficult to meter and direct the liquid in a precise fashion. This is particularly true in coloring facial hair, where the coloring needs to be applied in very precise, specific areas.

Application of liquids such as antiperspirants using a roller ball is well known. In this application, the ball is held in a compartment, and as it rolls along a surface, it picks up liquid from the compartment and deposits it on the surface in a precise and limited manner. With a roller ball application, there is very little chance of dripping or over-application.

Hair coloring often requires the mixing of two separate liquids immediately prior to application: the color, plus a developer. It would be desirable to provide a way to mix these two liquids and apply it to one's hair using a roller ball application, all in one step.

SUMMARY OF THE INVENTION

It is therefore an object of the invention to provide an applicator for hair color that can mix the color and developer and apply the mixed formula in a precise and simple fashion.

It is another object of the invention to provide an apparatus for hair color application that is simple and inexpensive to manufacture.

These and other objects are accomplished by an apparatus for applying a two-component liquid composition to a surface has a housing having an open end, an inner surface and an outer surface, an applicator retained in the housing and projecting through the open end, two containers removably mounted to the inner surface of the housing, each container having a dispensing nozzle extending through an aperture in the housing and arranged adjacent the applicator. There is a cutting device arranged on the housing adjacent the nozzles, the cutting device having at least one blade, wherein pressing the cutting device causes the blade to pierce the nozzles and allow contents of the containers to exit the containers and flow to the applicator.

In a preferred embodiment, the containers have flexible sidewalls, such that squeezing the containers causes the contents to flow more quickly onto the applicator. Alternatively, the containers could be rigid and actuated via a plunger mechanism on their ends.

There can be an outer covering surrounding both containers and attached to the housing to give the applicator a unified look and keep the containers in place in the housing.

The applicator can be any suitable applicator, such as a roller ball, a pad or a brush. A roller ball is ideal, because the two liquids are mixed as the roller ball is rolled onto the surface. The roller ball can also be equipped with a texture or grooves to enhance the mixing. Other options are a brush, a foam pad or a comb, particularly a hollow comb in which the substances travel through the teeth of the comb and are extruded through tips of the comb teeth.

While any two liquid or pasty substances could be dispensed, the containers are particularly suitable for holding hair coloring and developer for the hair coloring.

To enable mounting of the container onto the housing, the container is preferably connected to a holding tray that is removably snapped into the housing. Both the housing and holding tray are equipped with concentric apertures through which the nozzle extends toward the applicator.

In a preferred embodiment, the cutting mechanism comprises a button that is mounted on an aperture in the housing with the blade extending into the housing. Pressing the button causes the blade to extend farther into the housing and pierce the nozzle. Other cutting mechanisms, such as a rotatable blade, could also be envisioned. In a preferred embodiment, there are two cutting mechanisms, each mechanism having one blade configured to pierce a respective one of the nozzles. This way the cutting mechanisms can be activated independently, so that the substances in the containers can be dispensed at different times if desired.

While the invention is ideal for application of hair coloring, it could also be used for application of other products as well.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 9 shows an alternative embodiment of the invention, and

FIG. 10 shows another alternative embodiment of the invention.

DETAILED DESCRIPTION OF THE PREFERRED EMBODIMENT

Figure 1:
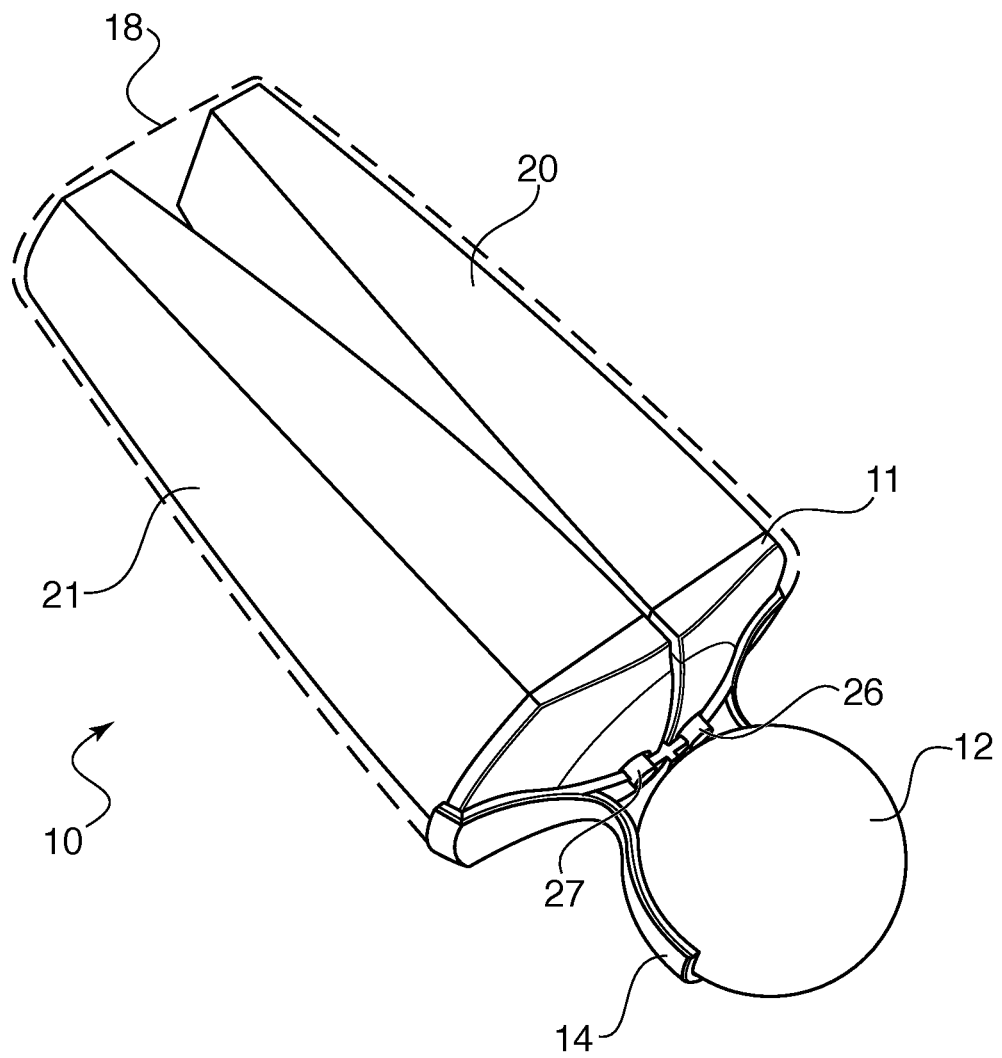
FIG. 1 shows a perspective view of the apparatus according to the invention with the outer covering shown in broken lines for ease of illustration.
Figure 2:
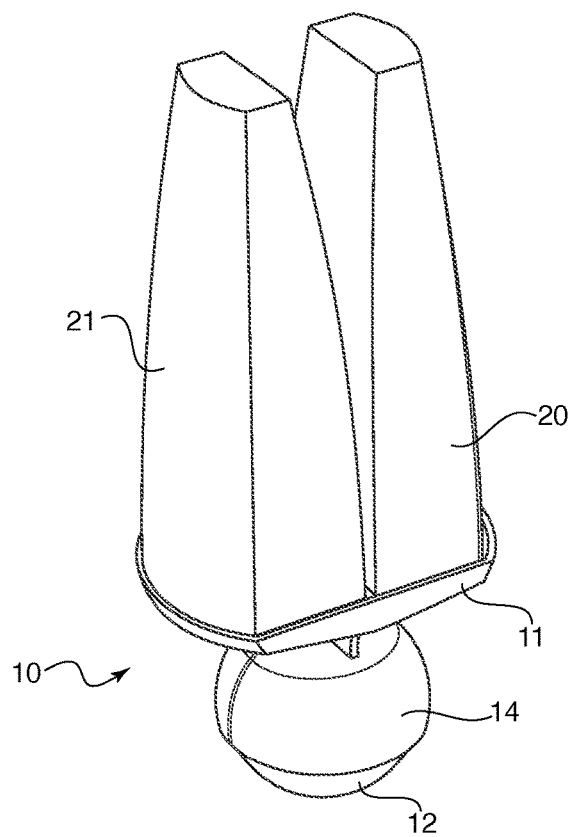
FIG. 2 shows the apparatus without the outer covering.
Figure 3:
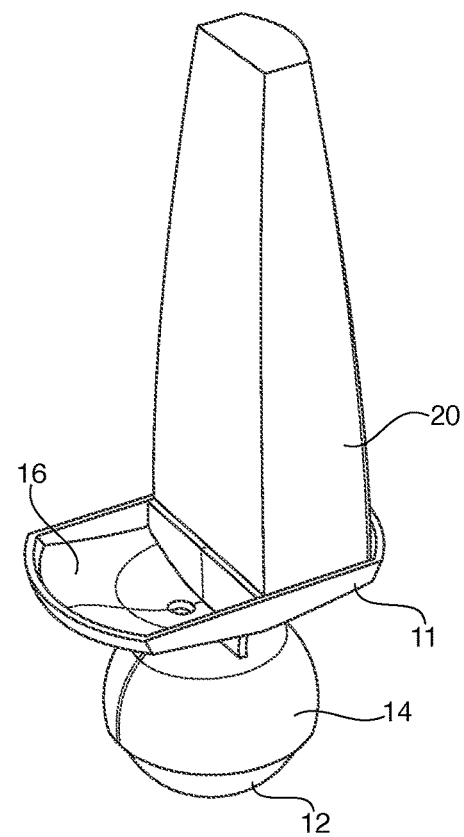
FIG. 3 shows the apparatus with one container removed.

Referring now in detail to the drawings, FIGS. 1-8b show a first embodiment of the applicator 10 according to the invention. Applicator 10 consists of a housing 11 that secures a roller ball 12 via a securing portion 14, which extends just past a circumferential midpoint of roller ball 12, so that roller ball 12 is securely retained inside securing portion 14. Two containers 20, 21 are disposed connected to the interior 16 of housing 11 as shown in FIG. 3 and are surrounded by an outer covering 18 as shown in FIG. 1. Containers 20, 21 contain liquid substances (not shown). These substances can be a hair colorant and a developer, or any other types of liquids that should be mixed upon application.

Figure 4:
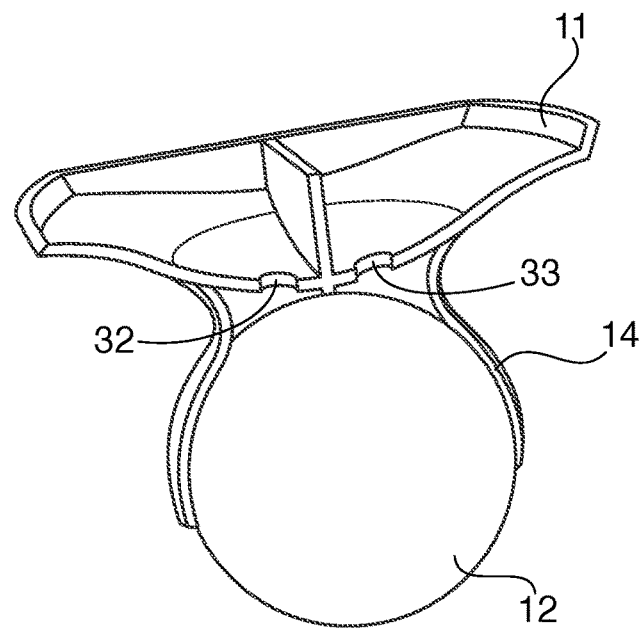
FIG. 4 shows a cut-away view of the roller ball and housing.
Figure 5:
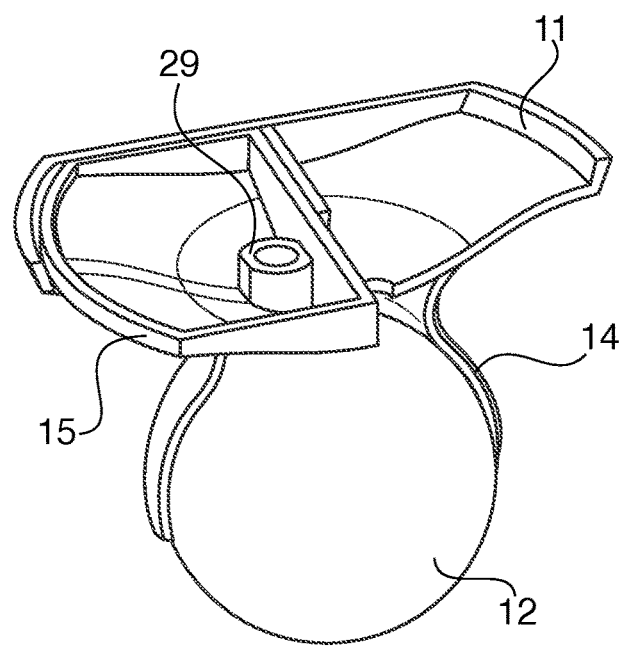
FIG. 5 shows a partial cut-away view of the roller ball and housing with one of the holding trays attached.

Containers 20, 21 have nozzles 26, 27, respectively, each located at a bottom of containers 20, 21, and which are directed downward and through apertures 32, 33 in housing 11 as shown in FIGS. 1 and 4. The liquid substances flowing out of nozzles 26, 27 contact roller ball 12 in such a manner that they are mixed together as the ball rolls along a surface. Containers 20, 21 hold the substances in an air-tight manner, so they do not dry out and do not flow through nozzles 26, 27 unless pressure is applied to containers 20, 21. In the embodiment of FIGS. 1 and 5, this pressure can be applied by squeezing the containers, which are constructed out of a flexible material. Other ways, such as the use of a plunger, could also be used.

As shown in FIG. 5, a holding tray 15 is disposed in housing 11 for connecting container 21 to housing 11. Each holding tray 15 is removably snapped into housing 11 to secure containers 21 to housing 11. Holding tray 15 has a channel 29 for receiving nozzle 27 of container 21. A second holding tray is disposed on the other side of housing 11 to receive container 20 in the same manner.

Figure 6:
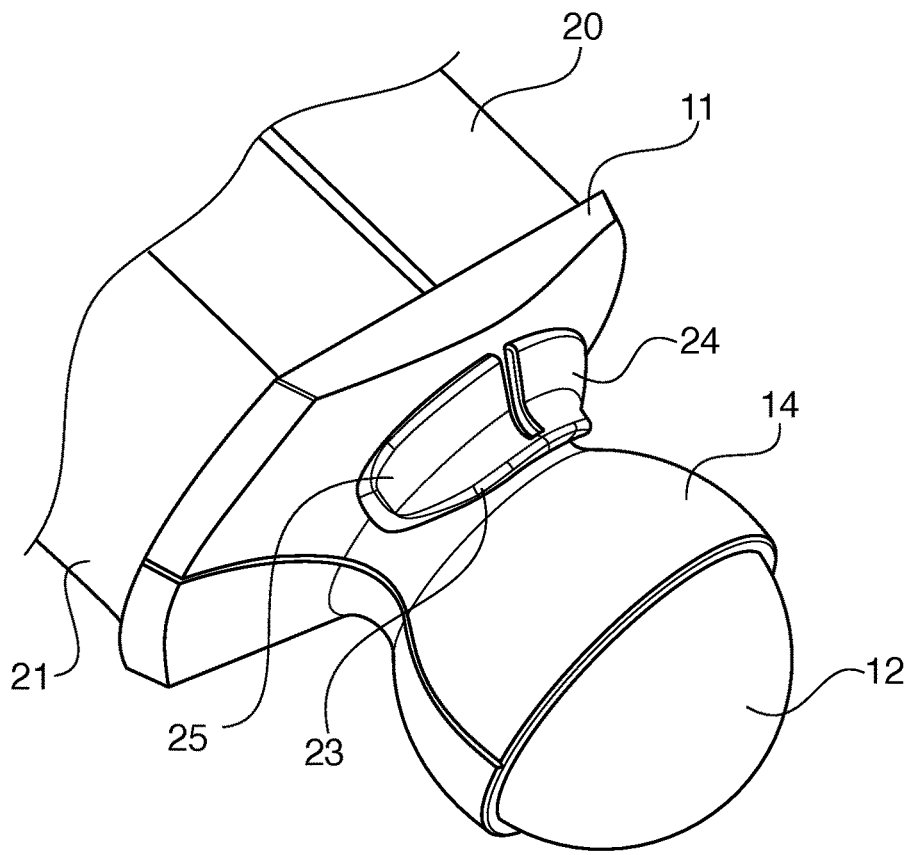
FIG. 6 shows an enlarged view of the apparatus completely assembled.
Figure 7:
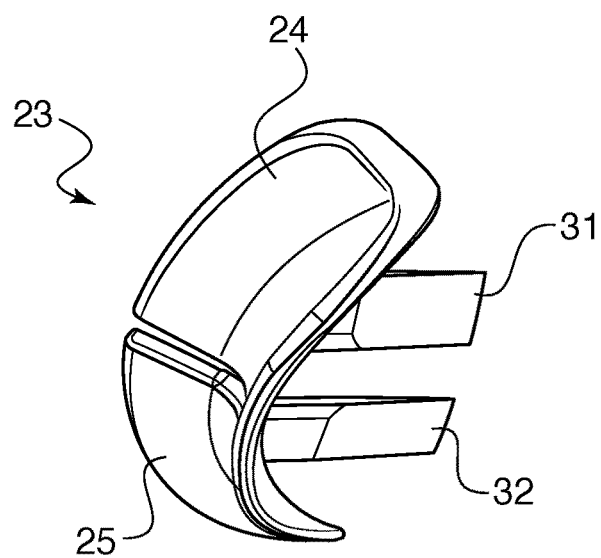
FIG. 7 shows the piercing device.
Figure 8A:
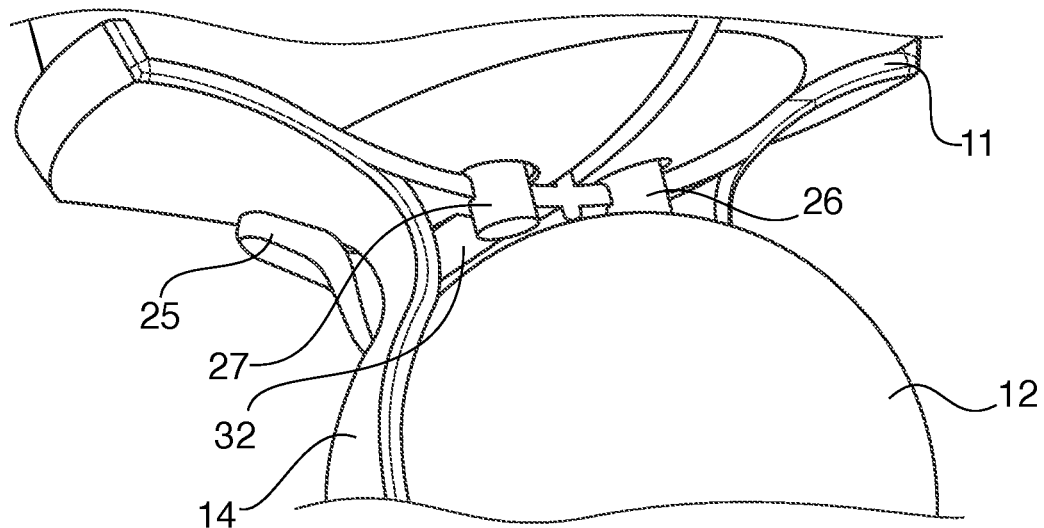
FIG. 8a shows an enlarged view of the assembled apparatus with one half removed for ease of illustration.
Figure 8B:
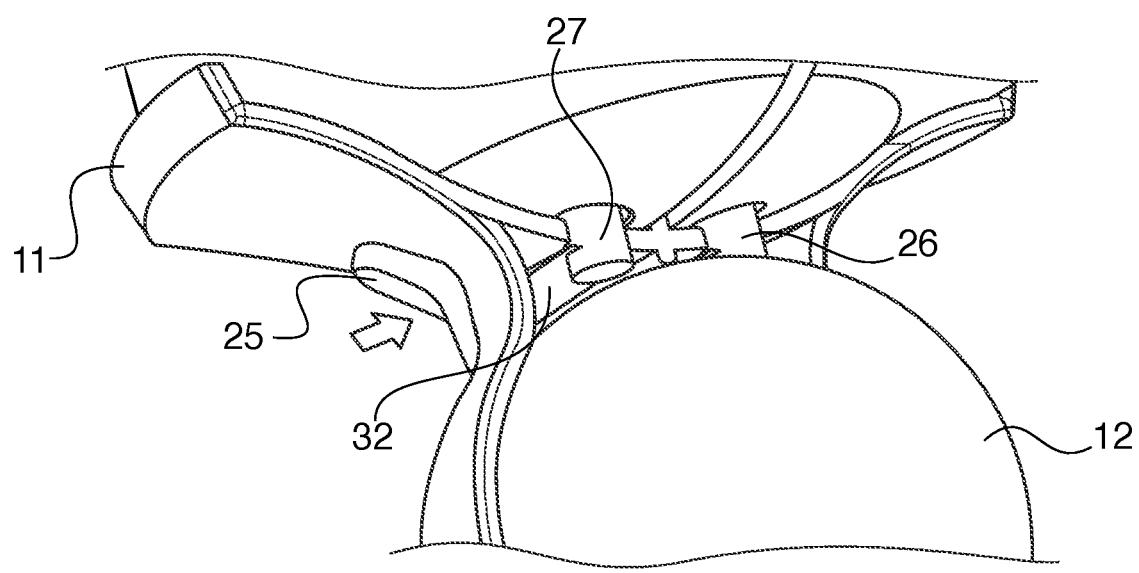
FIG. 8b shows the view of FIG. 8a with the piercing device piercing the colorant nozzles.

When containers 20, 21 are first connected to housing 11, nozzles 26, 27 are sealed so that no liquid can flow out. However in order to open these nozzles, a cutting device 23 as shown in FIGS. 6 and 7 is connected to housing 11 and acts on nozzles 26, 27 via an aperture in housing 11. Cutting device 23 is formed of a one-piece device that is slit down the middle into two independently actuatable buttons 24, 25, each of which is connected to a blade 31, 32, respectively. As shown in FIGS. 8a, and 8b, pressing on button 25 moves blade 32 toward and into nozzle 27, cutting it and allowing the contents of container 21 to be released onto roller ball 12. The same arrangement applies to button 24 and blade 31, as it cuts nozzle 26. The two buttons are independently actuatable so that only one nozzle can be cut if desired. Cutting device 23 utilizes the spring force of the plastic of which device 23 is made. Alternatively, buttons 24, 25 could be set into the device 23 using separate springs.

Alternative embodiments of the applicator are shown in FIGS. 9 and 10. In FIG. 9, the applicator is a brush 41 instead of a roller ball. In FIG. 10, the applicator is a sponge 42. The disbursement of liquid from containers 20 and 21 is the same as described above with respect to FIGS. 1-8a. Alternatively and not shown, the applicator could be a comb having hollow teeth so that the substances are extruded through the tips of the teeth of the comb.

The present invention provides a simple and effective way to apply a two-component hair coloring agent or other substance to a surface. The containers can be easily snapped in to the housing so that they can be interchanged or disposed of. The outer covering is optional or removable as desired. The entire applicator can be made of plastic and can be disposable or reusable (except for the containers, which are disposable).

Accordingly, while only a few embodiments of the present invention have been shown and described, it is obvious that many changes and modifications may be made thereunto without departing from the spirit and scope of the invention.

What is claimed is:

1. An apparatus for applying a two-component liquid composition to a surface, comprising:
   a housing having an open end, an inner surface and an outer surface;
   an applicator retained in the housing and projecting through the open end;
   two containers removably mounted to the inner surface of the housing, each container having a dispensing nozzle extending through an aperture in the housing and arranged adjacent the applicator;
   a cutting device arranged on the housing adjacent the nozzles and having at least one blade, wherein actuating the cutting device causes the at least one blade to pierce at least one of the nozzles and allow contents of at least one of the containers to and flow to the applicator.

2. The apparatus according to claim 1, wherein the containers have flexible sidewalls, such that squeezing the containers causes the contents to flow more quickly onto the applicator.

3. The apparatus according to claim 1, further comprising an outer covering surrounding both containers and attached to the housing.

4. The apparatus according to claim 1, wherein the applicator is selected from the group consisting of a roller ball, a pad and a brush.

5. The apparatus according to claim 1, wherein one container holds hair coloring and the other container holds developer for the hair coloring.

6. The apparatus according to claim 1, wherein each container is connected to a holding tray that is removably snapped into the housing to connect the container to the housing.

7. The apparatus according to claim 1, wherein the cutting device comprises a button that is mounted on an aperture in the housing with the at least one blade extending into the housing, wherein pressing the button causes the at least one blade to extend farther into the housing and pierce at least one of the nozzles.

8. The apparatus according to claim 1, wherein there are two buttons and two blades on the cutting device, each button being configured to move a corresponding one of the blades to pierce a corresponding one of the nozzles.

* * * * *